(12) United States Patent
Stelzig et al.

(10) Patent No.: US 9,668,944 B2
(45) Date of Patent: *Jun. 6, 2017

(54) DENTAL COMPOSITION

(71) Applicant: DENTSPLY INTERNATIONAL INC., York, PA (US)

(72) Inventors: Simon Stelzig, Constance (DE); Joachim E. Klee, Radolfzell (DE); Andreas Facher, Gundetswil (CH); Christoph Weber, Constance (DE)

(73) Assignee: Dentsply International Inc., York, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/704,301

(22) Filed: May 5, 2015

(65) Prior Publication Data

US 2015/0231040 A1    Aug. 20, 2015

Related U.S. Application Data

(63) Continuation of application No. 13/979,815, filed as application No. PCT/EP2011/005233 on Oct. 18, 2011, now abandoned.

(30) Foreign Application Priority Data

Oct. 19, 2010 (EP) ..................................... 10013769

(51) Int. Cl.
  *A61K 6/08* (2006.01)
  *A61K 6/00* (2006.01)

(52) U.S. Cl.
  CPC .............. *A61K 6/0091* (2013.01); *A61K 6/08* (2013.01)

(58) Field of Classification Search
  CPC ............................ A61K 6/0088; A61K 6/083
  USPC ......................................... 523/116; 433/228.1
  See application file for complete search history.

(56) References Cited

U.S. PATENT DOCUMENTS

| | | | |
|---|---|---|---|
| 2,768,992 A | 10/1956 | Zukas | |
| 3,655,605 A | 4/1972 | Smith et al. | |
| 3,814,717 A | 6/1974 | Wilson et al. | |
| 4,016,124 A | 4/1977 | Crisp et al. | |
| 4,035,321 A | 7/1977 | Shahidi et al. | |
| 4,089,830 A | 5/1978 | Tezuka et al. | |
| 4,143,018 A | 3/1979 | Crisp et al. | |
| 4,209,434 A | 6/1980 | Wilson et al. | |
| 4,317,681 A | 3/1982 | Beede et al. | |
| 4,342,677 A | 8/1982 | Muramatsu et al. | |
| 4,360,605 A | 11/1982 | Schmitt et al. | |
| 4,374,936 A | 2/1983 | Tomioka et al. | |
| 4,376,835 A | 3/1983 | Schmitt et al. | |
| 4,518,749 A | 5/1985 | Waddill et al. | |
| 5,104,962 A | 4/1992 | Yamaya et al. | |
| 5,130,347 A | 7/1992 | Mitra | |
| 5,154,762 A | 10/1992 | Mitra et al. | |
| 5,332,429 A * | 7/1994 | Mitra .................. | A61K 6/0088 106/35 |
| 5,334,681 A * | 8/1994 | Mueller .............. | C08F 290/062 351/159.33 |
| 5,559,185 A * | 9/1996 | Abe ........................ | C08L 51/04 525/132 |
| 6,953,832 B2 | 10/2005 | Moszner et al. | |
| 7,649,022 B2 * | 1/2010 | Gomurashvili ........ | A61K 31/74 424/442 |
| 2003/0232944 A1 | 12/2003 | Molenberg et al. | |
| 2005/0256223 A1 | 11/2005 | Kolb et al. | |
| 2005/0261393 A1 | 11/2005 | Mikulla et al. | |
| 2007/0293642 A1 | 12/2007 | Klee et al. | |

FOREIGN PATENT DOCUMENTS

| | | |
|---|---|---|
| DE | 19607641 A1 | 9/1997 |
| DE | 10058829 A1 | 6/2002 |
| DE | 10058830 A1 | 6/2002 |
| EP | 0797972 A2 | 10/1997 |
| EP | 2058318 A1 | 5/2009 |
| JP | 2005065902 A | 3/2005 |
| JP | 2006512466 A | 4/2006 |
| WO | 92/21632 A2 | 12/1992 |
| WO | 95/27008 A1 | 10/1995 |
| WO | 00/05182 A1 | 2/2000 |
| WO | 02/41845 A1 | 5/2002 |
| WO | 02/092021 A1 | 11/2002 |
| WO | 03/013444 A1 | 2/2003 |
| WO | 03/035013 A1 | 5/2003 |
| WO | 2008121895 A1 | 10/2008 |

* cited by examiner

*Primary Examiner* — Tae H Yoon
(74) *Attorney, Agent, or Firm* — McNees Wallace & Nurick LLC

(57) ABSTRACT

Dental composition comprising (i) a particulate filler; (ii) a polymerizable hydrolysis-stable compound of the following formula (1) $AX_n$ wherein A is a linker group containing at least n nitrogen atoms and optionally one or more acidic groups, X are moieties containing a polymerizable double bond and forming an amide bond with a nitrogen atom of A, which X may be the same or different and are represented by the following formula (2) wherein $R^1$ and $R^2$ are independent from each other and represent a hydrogen atom, a $C_{1-6}$ alkyl group or a group $-(CH_2)_m-Z$, wherein Z is COOM, $OPO_3M_2$, $PO_3M_2$, $SO_3M$, and M is independently a hydrogen atom or a metal atom, and m is an integer of from 0 to 6, L is a bond, a $C_{1-6}$ alkylene group; and n is an integer of at least 1; provided that at least one X cannot be a (meth)acryl group; and (iii) an initiator system.

18 Claims, No Drawings

DENTAL COMPOSITION

REFERENCE TO RELATED APPLICATION

This is a continuation application of U.S. patent application Ser. No. 13/979,815, now abandoned, having a 371(c) date of Oct. 22, 2013 and entitled "DENTAL COMPOSITION", which is a national stage entry of PCT/EP2011/005233, filed Oct. 18, 2011, and entitled "DENTAL COMPOSITION".

FIELD OF THE INVENTION

The present invention relates to a dental composition containing a specific hydrolysis-stable compound. The dental composition may be self-adhesive. Moreover, the present invention relates to the use of the specific hydrolysis-stable compound for the preparation of a dental composition, in particular a dental restorative or dental prosthetic composition. The dental compositions of the present invention are nontoxic and give superior adhesion to dentin, enamel and bone. The specific hydrolysis-stable compound of the present invention is resistant to an acidic medium so that dental composition of the present invention may be formulated as a one-component composition, for example as cavity liner and bonding materials and filling materials, which may be self-adhesive.

BACKGROUND OF THE INVENTION

Hard dental tissue having suffered large damage due to dental caries or the like, is conventionally restored by a procedure in which an indirect restoration such as a crown, a bridge, an inlay, or an onlay, is adhered on the damaged portion of the hard dental tissue with a specific dental composition such as a dental resin cement. Conventionally, a primer is required as a pre-treatment agent in order to improve adhesion of the resin cement to the dental hard tissue.

Alternatively, damaged hard dental tissue may be restored by using a direct restorative material which is applied as an uncured dental composition such as a dental composite, and hardened. Also in case of a dental composite, a primer is often required as a pre-treatment agent in order to improve adhesion of the dental composite to the dental hard tissue.

A dental resin cement and a dental composite are required to have sufficient adhesive and a material strength. Otherwise, not only the dental composition may be released from the hard dental tissue after some time under the severe conditions of the oral environment, but also a gap may be produced at an interface between the dental composition and the teeth, and bacteria may invade onto the exposed surfaces and impose an adverse effect on dental pulp.

The dental hard tissue is composed of enamel and dentin, and adhesion of the dental composition to both of them is clinically required. The primer for pre-treating a tooth surface has been conventionally used prior to application of a dental restorative composition for enhancing adhesion by demineralizing the tooth surface for making it rough and facilitating infiltration of the resin into a fine rough surface. Accordingly, when the dental composition is cured by chemical polymerization or photopolymerization, the adhesion to the hard dental tissue may be improved.

Given that the use of a dental primer increases complexity of a dental procedure, a simple adhesion procedure is desired which uses a self-adhesive dental composition which does not require a primer treatment for such various adherends.

Moreover, since adhesion of a dental composition to hard dental tissue requires the presence of acidic groups in the composition, the dental composition desireably has a high hydrolysis stability in order to avoid degradation of the composition during storage or when applied to hard dental tissue.

Japanese Patent Publication No. 2006-512466A discloses a self-adhesive resin cement which does not require the primer, that is a polymerizable composite material comprising at least one multifunctional monomer containing an acid in a concentration range of about 10-85% by weight, a non-reactive filler in a concentration range of about 1-80% by weight, a polymerization system in a concentration range of about 1.5-25% by weight, and water in a concentration range of about 0.1-25% by weight. However, since such the composition uses a single acidic monomer, sufficient adherability cannot be attained for both of inorganic component-rich enamel and organic component- and water-rich dentin.

International Publication No. WO 02/092021A1 discloses a self-adhesive dental composition consisting of a liquid and a powder. The resin cement consisting of the liquid and the powder, i.e. a powder-liquid type resin cement, is inferior in manipulability upon mixing as compared with a paste-and-paste type resin cement.

Japanese Patent Publication No. 2005-65902A discloses a dental adhesive composition comprising, as an essential adhesive component, a carboxylic acid compound having one (meth)acryloyl group and one carboxyl group which are bound to an aromatic group as a polymerizable monomer containing a particular carboxylic acid group. However, such the polymerizable monomer having an ester group quickly degrades in an acidic medium.

Dental materials based on polyfunctional amides are known from U.S. Pat. No. 6,953,832 which contain specific polymerizable amides and optionally strongly acidic polymerizable monomers such as dipentaerythritol pentamethacryloyloxy dihydrogenphosphate. Filler containing compositions are suggested. However, U.S. Pat. No. 6,953,832 does not disclose a self-adhesive composite.

WO92/21632 discloses a mixture of the following isomers of an ethylenically-unsaturated acidic alkoxysilane $H_2C=C(COOH)CH_2C(O)NH(CH_2)_3Si(OC_2H_5)_3$ and $H_2C=C(CH_2COOH)C(O)NH(CH_2)_3Si(OC_2H_5)_3$. The mixture is hydrolysed in a treatment solution further containing ethanol and water for treating the surface of a glass powder. The surface treated glass powder is used in a cement composition. Therefore, WO92/21632 neither discloses a hydrolysis-stable ethylenically-unsaturated monomer nor a dental composition comprising a particulate filler and a polymerizable hydrolysis-stable ethylenically-unsaturated monomer.

WO2008/121895 discloses a compound of the following formula:

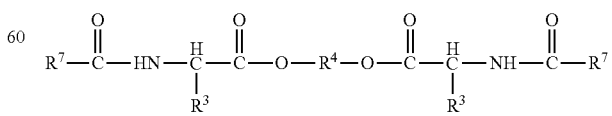

wherein, the Rs in each n monomer are independently selected from the group consisting of hydrogen, (C1-C6) alkyl, (C2-C6) alkenyl, (C2-C6) alkynyl, (C6-C10) aryl (C1-C6) alkyl and $(CH_2)_2SCH_3$; $R^4$ is independently selected from the group consisting of (C2-C20) alkylene, (C2-C20) alkenylene, (C2-C8) alkyloxy (C2-C20) alkylene, bicyclic-fragments of 1,4:3,6-dianhydrohexitols, and combinations thereof; and $R^7$ is independently selected from the group consisting of —CH=$CH_2$, —C($CH_3$)=$CH_2$, —CH=CH—($C_6H_5$), and —CH=CH—COOH. These compounds cannot be considered to be hydrolysis-stable given the ester groups essentially present in the molecule.

SUMMARY OF THE INVENTION

It is an object of the present invention to provide dental compositions, in particular dental composites, which are useful as filling materials, cavity liners and bases, cements, pit and fissure sealants to prevent caries, as adhesive between tooth structure and/or bone and polymeric composites, whereby the dental composition has excellent storage stability and long term mechanical resistance, and whereby the composition may be applied directly on the dental surface as a one-pack composition without prior application of a primer.

A further object is to provide dental restorative/prosthetic compositions that are relatively inexpensive and easy to manufacture.

The present invention provides a dental composition comprising
(i) a particulate filler;
(ii) a polymerizable hydrolysis-stable compound of the following formula (1), $$AX_n \quad (1)$$

wherein
A is a linker group containing at least n nitrogen atoms and optionally one or more acidic groups,
X are moieties containing a polymerizable double bond and forming an amide bond with a nitrogen atom of A, which X may be the same or different and are represented by the following formula (2)

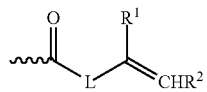

(2)

wherein
$R^1$ and $R^2$ are independent from each other and represent a hydrogen atom, a $C_{1-6}$ alkyl group or a group —$(CH_2)_m$—Z, wherein Z is COOM, $OPO_3M_2$, $PO_3M_2$, $SO_3M$, and M is independently a hydrogen atom or a metal atom, and m is an integer of from 0 to 6,
L is a bond, a $C_{1-6}$ alkylene group; and
n is an integer of at least 1;
provided that at least one X cannot be a (meth)acryl group; and
(iii) an initiator system.

In a specific embodiment, $R^1$ and $R^2$ in formula (2) are independent from each other and represent a hydrogen atom, a $C_{1-6}$ alkyl group or a group —$(CH_2)_m$—COOM, wherein M is hydrogen atom or a metal atom, and m is an integer of from 0 to 6.

Moreover, the present invention provides a use of the compound of formula (1) as defined above for the preparation of a dental composition.

Moreover, the present invention provides a process for preparing a compound of formula (1) as defined above, which comprises a step of a step-growth polymerization of a mixture containing a diamine of the following formula (3) and a compound of the following formula (4) having at least two carboxylic acid groups, said carboxylic acid groups may be present in the form of an anhydride, optionally in the presence of a compound of the following formula (5):

$$R^3(NHR')_y \quad (3)$$

wherein
$R^3$ represents an y-valent $C_{2-20}$ straight-chain, branched or cyclic hydrocarbon group which may optionally contain from 1 to 6 heteroatoms selected from nitrogen, oxygen, or sulphur atoms in the backbone of the hydrocarbon group, and optionally from 1 to 6 functional groups selected from hydroxyl groups, thiol groups and amino groups;
R' represents a hydrogen atom or a substituted or unsubstituted aliphatic or cycloaliphatic hydrocarbon group; and
y represents an integer of at least 2;

$$MOOC—R^4—COOM \quad (4)$$

wherein $R^4$ represents a $C_{1-20}$ straight-chain, branched, cyclic or aromatic hydrocarbon group which may optionally contain from 1 to 6 heteroatoms selected from nitrogen, oxygen, or sulphur atoms in the backbone of the hydrocarbon group, and optionally from 1 to 6 functional groups selected from carboxylic acid groups, hydroxyl groups, thiol groups and amino groups and the M, which may be the same or different, independently represent a hydrogen atom or a metal atom;

(5)

wherein L, $R^1$ and $R^2$ are as defined in claim 1, and Y is a leaving group or Y forms an intramolecular anhydride group together with a carboxyl group present in R' or $R^2$ and the adjacent carbonyl group.

The dental compositions according to the invention contain a mixture of hydrolysis-stable polymerizable components including a compound of formula (1). The mixture contains at least one acidic polymerizable monomer. Preferably, the mixture contains at least a crosslinking polymerizable monomer and an acidic polymerizable monomer. The polymerizable monomers are hydrolysis-stable. Specifically, the polymerizable monomers do not contain groups such as ester groups, in the main chain which hydrolyze in aqueous media at pH 3 at room temperature within one month.

DESCRIPTION OF THE PREFERRED EMBODIMENTS

The dental composition according to the present invention comprises a particulate filler. In a specific embodiment, the particulate filler is reactive with a polyacid in a cement reaction. A "particulate filler" is a powdered metal oxide or hydroxide, mineral silicate, or ion leachable glass or ceramic.

Examples of reactive particulate filler materials include materials commonly known in the art of dental compositions such as calcium or strontium-containing and aluminum-containing materials. Preferably, particulate reactive fillers contain leachable fluoride ions. Specific examples of particulate reactive fillers are selected from calcium alumino silicate glass, calcium alumino fluorosilicate glass, calcium aluminumfluoroborosilicate glass, strontium aluminosilicate glass, strontium aluminofluorosilicate glass, strontium aluminofluoroborosilicate glass. Suitable particulate reactive fillers further include metal oxides such as zinc oxide and magnesium oxide, and ion-leachable glasses, e.g., as described in U.S. Pat. No. 3,655,605, U.S. Pat. No. 3,814,717, U.S. Pat. No. 4,143,018, U.S. Pat. No. 4,209,434, U.S. Pat. No. 4,360,605 and U.S. Pat. No. 4,376,835.

Suitable non-reactive fillers may be selected from fillers currently used in dental restorative compositions.

The filler may have a unimodal or polymodal (e.g., bimodal) particle size distribution. The filler can be an inorganic material. It can also be a crosslinked organic material that is insoluble in the polymerizable resin, and is optionally filled with inorganic filler. The filler can be radiopaque, radiolucent or non-radiopaque. Examples of suitable non-reactive inorganic fillers are naturally-occurring or synthetic materials such as quartz, nitrides such as silicon nitride, glasses derived from, for example Ce, Sb, Sn, Zr, Sr, Ba and Al, colloidal silica, feldspar, borosilicate glass, kaolin, talc, titania, and zinc glass, and submicron silica particles such as pyrogenic silicas. Examples of suitable non-reactive organic filler particles include filled or unfilled pulverized polycarbonates or polyepoxides. Preferably the surface of the filler particles is treated with a coupling agent in order to enhance the bond between the filler and the matrix. The use of suitable coupling agents include gamma-methacryloxypropyltrimethoxysilane, gamma-mercaptopropyltriethoxysilane, gamma-aminopropyltrimethoxysilane, and the like.

The particulate filler usually has an average particle size of from 0.005 to 100 μm, preferably of from 0.01 to 40 μm as measured using, for example, by electron microscopy or by using a conventional laser diffraction particle sizing method as embodied by a MALVERN Mastersizer S or MALVERN Mastersizer 2000 apparatus. The particulate filler may be a multimodal particulate reactive filler representing a mixture of two or more particulate fractions having different average particle sizes. The particulate reactive filler may also be a mixture of particles of different chemical composition. In particular, it is possible to use a mixture of a particulate reactive material and a particulate non-reactive material. The particulate reactive filler may be surface modified by a surface modifying agent.

Moreover, the dental composition of the present invention comprises a polymerizable hydrolysis-stable compound of the following formula (1).

$$AX_n \quad (1)$$

The polymerizable compounds of formula (1) comprise a moiety A, and at least one substituent X. In formula (1), A is a linker group containing at least n nitrogen atoms and optionally one or more acidic groups. The linker has a valency of at least one which corresponds to the total number of substituents X. Accordingly, A may be preferably monovalent (n=1), divalent (n=2), trivalent (n=3), tetravalent (n=4), pentavalent (n=5), or hexavalent (n=6). Preferable A is divalent or trivalent, most preferably divalent.

Preferably, the linker group is a linear or branched monomeric, oligomeric, polymeric or copolymeric group containing nitrogen atoms at the terminal positions for forming an amide bond with a moiety X. A monomeric groups is a low-molecular group having a molecular weight of up to 500. An oligomeric group is a group having a molecular weight of more than 500 to up to 10000 and may be prepared by a polymerization reaction. A polymeric or copolymeric group is a group having a molecular weight of more than 10000 which may be obtained by a polymerization reaction. The polymerization may be a condensation or addition reaction.

The linker A may be a hydrocarbon group which may be aliphatic and/or aromatic. The hydrocarbon group may be substituted by 1 to 6 $C_{1-4}$ alkyl groups. Specific examples of the alkyl groups are methyl, ethyl, n-propyl, i-propyl, n-butyl, i-butyl or tert.-butyl. In a preferred embodiment, the hydrocarbon group of the linker A may contain 1 to 5 oxygen atoms in the hydrocarbon group in the form of aliphatic or aromatic ether bonds, keto groups, carboxylic acid groups, or hydroxyl groups. Ester groups are not preferred in moiety A in view of hydrolysis stability of the polymerizable monomer. In case of an aliphatic group, A may be a straight chain or branched chain alkylene group or a cycloalkylene group. In case of an aromatic group, A may be an arylene group or a heteroarylene group. Specifically, A may be a divalent substituted or unsubstituted $C_1$ to $C_{20}$ alkylene group, substituted or unsubstituted $C_{6-14}$ arylene group, substituted or unsubstituted $C_3$ to $C_{20}$ cycloalkylene group, substituted or unsubstituted $C_7$ to $C_{20}$ arylenealkylenearylene group. Preferably, A represents a saturated aliphatic $C_{2-20}$ hydrocarbon chain which may contain 2 to 4 oxygen atoms or nitrogen atoms, and which may be substituted by 1 to 6 $C_{1-4}$ alkyl groups, or A may be a substituted or unsubstituted $C_7$ to $C_{20}$ arylenealkylenearylene group which may be substituted by 1 to 6 $C_{1-4}$ alkyl groups.

According to a preferred embodiment, the polymerizable compound of formula (1) contains one or more acidic groups selected from carboxylic acid groups, phosphonic acid groups, sulfonic acid groups or phosphoric acid ester groups.

Preferably, the linker group is a polyamide group obtainable by a process comprising a condensation or addition reaction of a mixture containing a diamine of the formula (3) and a compound of the formula (4) having at least two carboxylic acid groups, optionally in the presence of a compound of the above formula (5).

In formula (3), $R^3$ represents an y-valent $C_{2-20}$ straight-chain, branched or cyclic hydrocarbon group which may optionally contain from 1 to 6 heteroatoms selected from nitrogen, oxygen, or sulphur atoms in the backbone of the hydrocarbon group, and optionally from 1 to 6 functional groups selected from hydroxyl groups, thiol groups and amino groups.

In formula (3), R' represents a hydrogen atom or a substituted or unsubstituted aliphatic or cycloaliphatic hydrocarbon group.

In formula (3), y represents an integer of at least 2.

In formula (4), $R^4$ represents a $C_{1-20}$ straight-chain, branched, cyclic or aromatic hydrocarbon group which may optionally contain from 1 to 6 heteroatoms selected from nitrogen, oxygen, or sulphur atoms in the backbone of the hydrocarbon group and optionally from 1 to 6 functional groups selected from carboxylic acid groups, hydroxyl groups, thiol groups and amino groups.

In formula (5), L, $R^1$ and $R^2$ are as defined above, and Y is a leaving group or Y forms an intramolecular anhydride group together with a carboxyl group present in $R^1$ or $R^2$ and the adjacent carbonyl group.

The carboxylic acid groups of a compound of formula (4) may be present in the form of an anhydride. The anhydride may be in intramolecular anhydride or an intermolecular anhydride. Accordingly, a carboxylic group of a compound of formula (4) may form an anhydride with a carboxylic acid group present in the same molecule or in a further molecule of formula (4). The carboxylic group of a compound of formula (4) may form an anhydride with a further carboxylic acid molecule. Suitable further carboxylic acids may be selected from acetic acid, propanoic acid, butanoic acid and the like.

According to a preferred embodiment, the linker group may be a polyoxyalkylene group containing nitrogen atoms at the terminal positions.

The polymerizable compound of formula (1) preferably has an average molecular weight of from 300 to 10,000, more preferably 500 to 7000.

In formula (1), X are moieties containing a polymerizable double bond and forming an amide bond with a nitrogen atom of A, which X may be the same or different and are represented by the following formula (2).

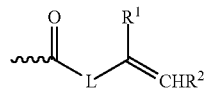

(2)

In formula (2), $R^1$ and $R^2$ are independent from each other and represent a hydrogen atom, a $C_{1-6}$ alkyl group or a group —$(CH_2)_m$—COOM, wherein M is hydrogen atom or a metal atom, and m is an integer of from 0 to 6. In a specific embodiment, $R^1$ and $R^2$ in formula (2) are independent from each other and represent a hydrogen atom, a $C_1$ alkyl group or a group —$(CH_2)_m$—COOM, wherein M is hydrogen atom or a metal atom, and m is an integer of from 0 to 6. Preferably, $R^1$ is single bond or a methyl group. Preferably, $R^2$ is a hydrogen atom or a group —$(CH_2)_m$—COOH, wherein m is 0, 1 or 2.

In formula (2), L is a bond or a $C_{1-6}$ alkylene group, preferably a single bond or a methylene or ethylene group.

In formula (1), n is at least 1. Preferably, n is an integer of at least 1 and less than 10, more preferably 2 to 6.

In a polymerizable compound of the formula (1), at least one X cannot be a (meth)acryl group.

The dental composition according to the present invention comprises an initiator system. The initiator system may be based on a redox initiator or on a photoinitiator.

In case the dental composition contains a redox initiator, the amount of reducing agent and oxidizing agent should be sufficient to provide the desired degree of polymerization. Preferably, the mixed but unset cements of the invention contain a combined weight of about 0.01 to about 10%, more preferably about 0.2 to about 5%, and most preferably about 0.3 to about 3% of the reducing agent and oxidizing agent, based on the total weight (including water) of the mixed but unset cement components. The reducing agent or the oxidizing agent can be microencapsulated as described in U.S. Pat. No. 5,154,762. This will generally enhance shelf stability of the cement parts and if necessary permit packaging both the reducing agent and oxidizing agent together. Water-soluble and water-insoluble encapsulants can be employed. Suitable encapsulating materials include cellulosic materials as cellulose acetate, cellulose acetate butyrate, ethyl cellulose, hydroxymethyl cellulose and hydroxyethyl cellulose being preferred. Other encapsulants include polystyrene, copolymers of polystyrene with other vinylic monomers and polymethylmethacrylate, copolymers of methylmethacrylate with other ethylenically-unsaturated monomers. Preferred encapsulants are ethylcellulose and cellulose acetate butyrate. By varying the choice of encapsulant and the encapsulation conditions, the onset of curing can be tailored to start at times ranging from seconds to minutes. The ratio of amount of encapsulant to activator generally ranges from 0.5 to about 10 and preferably from about 2 to about 6.

Suitable oxidizing agents (initiators) include peroxides such as benzoyl peroxide cumene hydroperoxide (CHP), and tert-butyl hydroperoxide, ferric chloride, hydroxylamine (depending upon the choice of reducing agent), perboric acid and its salts, and salts of a permanganate or persulfate anion. Preferred oxidizing agents are peroxides, potassium persulfate, ammonium persulfate and hydrogen peroxide.

Suitable reducing agents (activators) include ascorbic acid, benzyl thiourea ferrous chloride, ferrous sulfate, hydrazine, hydroxylamine (depending upon the choice of oxidizing agent) oxalic acid, thiourea, and salts of a dithionite or sulfite anion. Preferred reducing agents include ascorbic acid and ferrous sulfate.

A photoinitiator should be capable of promoting polymerization of the polymerizable groups on exposure to light of a suitable wavelength and intensity. The photoinitiator preferably is sufficiently shelf-stable and free of undesirable coloration to permit its storage and use under typical dental conditions. Visible light photoinitiators are preferred. Suitable visible light-induced and ultraviolet light-induced initiators include an alpha-diketone (e.g., camphorquinone) with or without additional hydrogen donors (such as sodium benzene sulfinate, amines and amine alcohols). The photoinitiator may be present in an amount sufficient to provide the desired rate of photopolymerization. This amount will be dependent in part on the light source, the thickness of the cement layer to be exposed to radiant energy and the extinction coefficient of the photoinitiator. Preferably, mixed but unset photocurable cements of the invention will contain about 0.01 to about 5%, more preferably from about 0.1 to about 2% photoinitiator, based on the total weight (including water) of the mixed but unset cement components.

The dental composition according to the present invention may contain further polymeric components, such as a polymer having acidic groups.

As used herein, the term "polymer" includes molecules whose backbone is derived from one monomer (viz. a homopolymer) or from two or more monomers (viz., a copolymer). A polymer typically has a weight average molecular weight of at least about 10000 Da. Polymerizable acids used for preparing polymers useful for glass-ionomer cement systems include alkenoic acids and unsaturated mono-, di- and tricarboxylic acids. Representative alkenoic acids are described, for example, in U.S. Pat. No. 4,016,124, U.S. Pat. No. 4,089,830, U.S. Pat. No. 3,655,605; U.S. Pat. No. 4,143,018; U.S. Pat. No. 4,342,677, U.S. Pat. No. 4,360,605, U.S. Pat. No. 4,376,835 and U.S. Pat. No. 5,130,347. Specific examples are acrylic acid, methacrylic acid, maleic acid, fumaric acid, itaconic acid, crotonic acid, and derivatives thereof, such as the acid chlorides thereof, the acid anhydrides thereof and chloro or bromo derivatives thereof. Particularly preferred monomers are acrylic acid, itaconic acid and maleic acid, and the chlorides or anhydrides thereof. The pendent carboxylic acid groups of the ionomer must be sufficient in number or percent by weight to bring about the setting or curing reaction in the presence of the modified particulate reactive and/or non-reactive filler.

Polymerizable double bonds as a source of additional covalent crosslinking, which imparts additional strength to the ultimate dental composition, may be introduced by reacting a portion of the carboxylic acid groups with a bi-functional monomer. Examples of suitable bi-functional monomers include bisacrylamides such as N,N'-diethyl-1,3-bisacrylamido-propan (BADEP), 1,3-bisacrylamido-propan (BAP), and 1,3-bisacrylamido-2-ethyl-propan (BAPEN); acryloyl chloride, methacryloyl chloride, vinyl azalactone, allyl isocyanate, 2-hydroxyethylmethacrylate (HEMA), 2-am inoethylmethacrylate, 2-isocyanatoethyl methacrylate (IEM), acrylic acid, methacrylic acid and N-vinylpyrrolidone. Other examples of suitable bi-functional monomers are described in U.S. Pat. No. 4,035,321 U.S. Pat. No. 5,130,347.

To effect cross-linking or additional cross-linking of the dental composition, one or more comonomers may be included in the dental composition. Suitable comonomers contain at least one polymerizable functional group. Suitable polymerizable functional groups are ethylenically unsaturated groups (e. g. alkenyl groups and preferably vinyl groups). Ethylenically unsaturated groups are polymerisable by a free radical mechanism. Preferred examples are substituted and unsubstituted acrylates, methacrylates, or alkenes.

A dental composition is prepared by mixing the components of the dental composition of the present invention. The components of the dental composition can be combined (such as by mixing or blending) in a variety of manners and amounts in order to form the dental composition of the present invention.

For example, a concentrated solution of the polymerizable compound, and the initiator system may be mixed with the particulate filler and optionally further components at the time of use.

Alternatively, the polymerizable compound, the initiator system, the particulate filler and optionally the ionomer are provided as a freeze-dried or lyophilized powdered blend under conditions in which there is not sufficient water to allow the setting reaction to proceed. Such systems can then be combined with water at the time of use in order to begin the setting reaction. Once the setting reaction has begun, the resultant mixture may be formed into its desired shape, followed by curing and allowing the mixture to fully harden.

In general, the weight-to-weight ratio of the ionomer to water is from about 1:10 to about 10:1. In general, the concentration of ionomer in water ranges from 25 to 75% by weight, and preferably from 40 to 65 percent. The resultant aqueous solution has a weight ratio of polymer to liquid (polymer:liquid) generally ranging from about 1.5 to 8.

The reaction mixture may also include a modifying agent such as tartaric acid, for adjusting the working time and a setting time, respectively, when preparing the cement as described in U.S. Pat. No. 4,089,830, U.S. Pat. No. 4,209,434, U.S. Pat. No. 4,317,681 and U.S. Pat. No. 4,374,936. In general, an increase in working time results in an increase in setting time as well.

The "working time" is the time between the beginning of the setting reaction when the ionomer and modified particulate reactive filler are combined in the presence of water, and the time the setting reaction proceeds to the point when it is no longer practical to perform further physical work upon the system, e.g. spatulate it or reshape it, for its intended dental or medical application.

The "setting time" is the time measured from the beginning of the setting reaction in a restoration to the time sufficient hardening has occurred to allow subsequent clinical or surgical procedures to be performed on the surface of the restoration.

In a setting reaction, due to the presence of polymerizable double bonds, a polymerization reaction takes place.

The dental compositions of the present invention may further contain solvents, pigments, nonvitreous fillers, free radical scavengers, polymerization inhibitors, bisacrylamides such as N,N'-diethyl-1,3-bisacrylamido-propan (BADEP), 1,3-bisacrylamido-propan (BAP), and 1,3-bisacrylamido-2-ethyl-propan (BAPEN), reactive and nonreactive diluents e.g., 2-hydroxyethyl methacrylate (HEMA), hydroxypropyl methacrylate, surfactants (such as to enhance solubility of an inhibitor e. g., polyoxyethylene), coupling agents to enhance reactivity of fillers e.g., 3-(trimethoxysilyl) propyl methacrylate, and rheology modifiers.

Suitable solvents or nonreactive diluents include alcohols such as ethanol and propanol. Suitable reactive diluents are alpha,beta unsaturated monomers for providing altered properties such as toughness, adhesion, and set time.

Suitable alpha,beta-unsaturated monomers may be acrylates and methacrylates such as methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bis-phenol A ("bis-GMA"), glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethylhexa methylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2- methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, and 2,2'-bis[3(4-phenoxy)-2-hydroxypropane-1-acryalte]propane, may be mentioned. Other suitable examples of polymerizable components are isopropenyl oxazoline, vinyl azalactone, vinyl pyrrolidone, styrene, divinylbenzene, urethane acrylates or methacrylates, epoxy acrylates or methacrylates and polyol acrylates or methacrylates. Mixtures of alpha,beta-unsaturated monomers can be added if desired. Preferably, the mixed but unset dental compositions of the invention will contain a combined weight of about 0.5 to about 40%, more preferably about 1 to about 30%, and most preferably about 5 to 20% water, solvents, diluents and alpha,beta-unsaturated monomers, based on the total weight (including such water, solvents, diluents and alpha,beta-unsaturated monomers) of the mixed but unset dental composition components.

An example of a suitable free radical scavenger is 4-methoxyphenol. An example of a suitable inhibitor is hydroxytoluene or butylated hydroxytoluene (BHT). The amount of inhibitor may be selected from 0.001 to 2% and preferably from 0.02 to 0.5% based on the total weight of the copolymer/comonomer/water mixture.

Depending upon the application of the dental composition and the manner in which polymerization is achieved, various components of the cement may be packaged differently. For example, in the case of a redox-based system, ingredients of the dental composition composition are divided into two separate packages—the first package containing the copolymer, comonomer, the initiator and water, and the second package containing the reactive filler and the activator. In another embodiment, the first package contains all solid materials (e.g., copolymer, comonomer, reactive filler and if desired, the reducing agent, and the second package contains water and if desired, the initiator. In the case of photo-initiation, the photo-initiator can be included in either the solid (e. g. paste) or liquid parts of the dental composition.

Preferably, the dental composition of the present invention is packaged as a one-pack composition wherein all components are combined in a single composition.

The process for the preparation of the polymerizable compound of the formula (1) according to the present invention comprises a step (i) of a step-growth polymerization of a mixture containing a diamine and a compound having at least two carboxylic acid groups or an anhydride thereof, optionally in the presence of a compound of the following formula (5) for obtaining a polyamide:

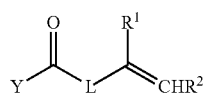

(5)

wherein L, $R^1$ and $R^2$ are as defined above, and Y is a leaving group or Y forms an intramolecular anhydride group together with a carboxyl group present in $R^1$ or $R^2$ and the adjacent carbonyl group, The process further comprises a step (ii) of introducing moieties of the formula (2) by reacting the polyamide obtained in step (i) with a compound of formula (5) wherein Y is a leaving group and $R^1$ and $R^2$ are as defined in claim 1.

Alternatively, the process for the preparation of the polymerizable compound of the formula (1) according to the present invention comprises a step (iii) of reacting a mixture containing a diamine and a compound of formula (5) for obtaining an amide and a step (iv) of a step-growth polymerization of a mixture containing the amide obtained in (iii) and a compound having at least two carboxylic acid groups or an anhydride thereof for obtaining the polymerizable compound of the formula (1).

Preferably, the diamine is a compound of the formula (3), $R^3(NHR')_y$, wherein $R^3$ represents an y-valent $C_{2-20}$ straight-chain, branched or cyclic hydrocarbon group which may optionally contain from 1 to 6 heteroatoms selected from nitrogen, oxygen, or sulphur atoms in the backbone of the hydrocarbon group, and optionally from 1 to 6 functional groups selected from hydroxyl groups, thiol groups and amino groups; R' represents a hydrogen atom or a substituted or unsubstituted aliphatic or cycloaliphatic hydrocarbon group; and y represents an integer of at least 2.

In the process according to the present invention, the compound having at least two carboxylic acid groups is preferably a compound of formula (4), (MOOC—$R^4$—COOM), wherein $R^4$ represents a $C_{1-20}$ straight-chain, branched, cyclic or aromatic hydrocarbon group which may optionally contain from 1 to 6 heteroatoms selected from nitrogen, oxygen, or sulphur atoms in the backbone of the hydrocarbon group, and optionally from 1 to 6 functional groups selected from carboxylic acid groups, hydroxyl groups, thiol groups and amino groups.

In the process according to the present invention, the compound of formula (5) is preferably itaconic acid or a lactone or a carboxylic anhydride thereof.

In a preferred embodiment, the polymerizable compound of the present invention is a compound of the formula (1a), $AX_n$, wherein A is a linker group containing at least n nitrogen atoms and optionally one or more acidic groups, X are moieties containing a polymerizable double bond and forming an amide bond with a nitrogen atom of A, wherein the X, which may be the same or different, are represented by the following formula (2a)

(2a)

wherein
$R^1$ and $R^2$ are independent from each other and represent a hydrogen atom, a $C_{1-6}$ alkyl group or a group —$(CH_2)_m$—COOM, wherein M is a hydrogen atom or a metal atom, and m is an integer of from 0 to 6, provided that at least one X cannot be a (meth)acryl group; L is a bond or a $C_{1-6}$ alkylene group; and n is an integer of at least 2.

A compound of formula (1) or (1a) according to the present invention may be used for the preparation of a dental composition. Specifically, the dental composition may comprise the polymerizable compound of the formula (1) or (1a), an initiator system, and optionally a particulate filler. The dental composition may be a dental adhesive composition or a dental composition composition.

The invention will now be further illustrated by the following Examples. All percentages refer to percentages by weight unless stated otherwise.

EXAMPLES

Example 1

Preparation of a Water-Soluble Polymerizable Compound of Formula (1):

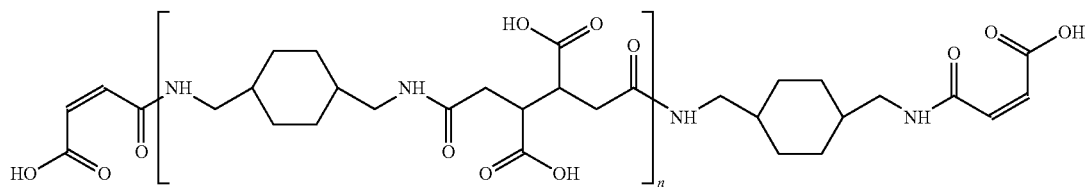

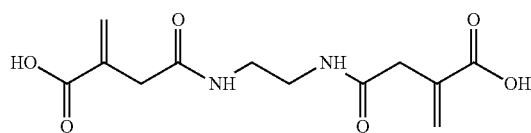 [SMILES: C=C(CC(=O)NCCNC(=O)CC(=C)C(=O)O)C(=O)O]

0.01 mol of ethylendiamine (CAS: 107-15-3) were dissolved in 15 mL chloroform. 0.021 mol itaconic acid anhydride are slurried in 7.5 mL chloroform and slowly added dropwise to the solution of the diamine. After completion of the dropwise addition, the reaction mixture is refluxed for 24 h. The solid obtained is filtered and washed with acetone (50 mL) and dried in vacuo. 2.2 g of a fine particulate white powder are obtained.

IR: $\nu$ (in cm$^{-1}$)=3311, 1682, 1647, 1630, 1544
$^1$H-NMR (DMSO-d$_6$, 400 MHz)=6,093/5,774 (d, 2H), 5,637/5,460 (d, 2H), 3,025/3,130/3,068 (s, 8H)

Example 2

Preparation of a Polymerizable Compound of Formula (1):

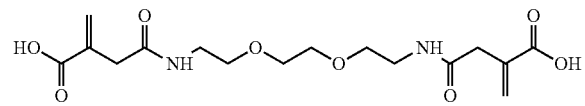 [SMILES: C=C(CC(=O)NCCOCCOCCNC(=O)CC(=C)C(=O)O)C(=O)O]

0.01 mol of 2,2'-(ethylenedioxy)bis(ethylamine) (CAS: 929-59-9) were dissolved in 15 mL chloroform. 0.021 mol itaconic acid anhydride are slurried in 7.5 mL chloroform and slowly added dropwise to the solution of the diamine. After completion of the dropwise addition, the reaction mixture is refluxed for 24 h. The solid obtained is filtered and washed with ethyl acetate (50 mL) and dried in vacuo. 1.7 g of a white solid are obtained.

IR: $\nu$ (in cm$^{-1}$)=3310, 1680, 1642, 1628, 1135 $^1$H-NMR (D$_2$O, 400 MHz)=6,254 (s, 2H), 5,754 (s, 2H), 3,553 (s, 4H), 3,503 (tr, 4H, $^3$J=5.2 Hz), 3,283 (tr, 4H, $^3$J=5.2 Hz), 3,185 (s, 4H) ppm.

Example 3

Preparation of a Macromonomeric Polymerizable Compound of Formula (1):

0.022 mol (3.16 g) of 1,4-cyclohexane bismethylamine are dissolved in 8 mL DMSO. 0.020 mol (3.96 g) butane tetracarboxylic acid dianhydride und 0.022 mol maleic acic anhydride (2.20 g) are dissolved in 36 mL DMSO. The two solutions are simultaneously added dropwise into a flask over the same period of time. During the addition, the reaction mixture is cooled on a water bath. BHT is added to this mixture as a stabilisor. The resulting reaction mixture is stirred at room temperature for 16 h. Subsequently, the product is precipitated twice in diethyl ether or tert.-butyl methylether and the resulting precipitate is dried in vacuo.

IR: $\nu$ (in cm$^{-1}$)=3288, 2939, 2872, 1717, 1649, 1546.
$^1$H-NMR (DMSO-d$_6$, 400 MHz)=9.051-7.780 (m, CONH), 6.393+6.199 (d, CH$_2$CCH$_3$COO, vinyl protons), 3.636-2.670 (m, backbone), 2.461-0.813 (m, backbone), ppm.

Application Example 1

8.2 g of the macromonomeric polymerizable compound of formula (1) obtained in Example 3 are mixed with 4.2 g diethyleneglycol dimethacrylat, 2.1 g 2-N,N'-bisacrylamido-N,N'-diethyl-1,3-propane, 0.186 g 2,6-di-tert-butyl-p-kresol, 0.062 g Camphor quinone und 0.210 g ethyl 4-dimethylaminobenzoate. The resulting mixture is stirred for 16 hours at room temperature, whereby a homogenous mixture is formed.

To 1.0 g of this mixture, 1.0 g of an inert silanated partiuculate bariumaluminosilicate glass was added and homogenized by stirring whereby a dental composite is obtained. The adhesion (SBS=shear bond strength) of the dental composite on enamel is 3.8±0.4 MPa.

The measurement of the adhesion was carried out according to the following procedure.

In order to provide a uniform surface, human teeth are treated by using a Struers Labo Pol-5 polishing device first with humidified SiC paper grit 220 and finally with humidified SiC-paper grit 500. For the determination of the adhesion to enamel, a surface portion having a radius of about 5 mm is of the enamel is polished and the tooth is rinsed with Conditioner 36 and etched for 15 seconds. Subsequently, the tooth is rinsed with water.

The tooth to be is embedded into a wax according to the Uhlig procedure so that the surface to be prepared is oriented horizontally upwards. The ground tooth surface is carefully dried with a cloth. The dental composite composition is placed on the tooth surface by using a two part mold and the mold is filled with a glass ionomer, compacted with a film and cured for 40 seconds at 500 mW/cm² by using a polymerisation light (Spectrum 800).

The tooth is then removed from the wax embedding and maintained for 1 h at 37° C. and 100% relative humidity. Subsequently, the samples are stored for 23 h in distilled water at 37° C.

For the measurement, the tooth are immobilized in a plastic tray by using plaster. Accordingly, 100 g gypsum are mixed with 30 g water. This mixture is entered into a mold. The teeth are inserted therein so that the adhesion surface is oriented perpendicular whereby the adhesionbody is kept at a distance from the plaster. The shear bond strength is then measured by using standard equipment.

We claim:

1. A dental composition comprising:
   (i) a dental particulate filler;
   (ii) a polymerizable hydrolysis-stable compound of the following formula (1), $$AX_n \quad (1)$$

wherein
   A is a linker group containing at least n nitrogen atoms and optionally one or more acidic groups,
   X are moieties containing a polymerizable double bond and forming an amide bond with a nitrogen atom of A, which X may be the same or different and are represented by the following formula (2)

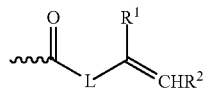
   (2)

wherein
   $R^1$ and $R^2$ are independent from each other and represent a hydrogen atom, a $C_{1-6}$ alkyl group, or a —$(CH_2)_m$—Z group, wherein Z is COOM, $OPO_3M_2$, $PO_3M_2$, or $SO_3M$, M is independently a hydrogen atom or a metal atom, and m is an integer of from 0 to 6,
   L is a bond or a C1-6 alkylene group; and
   n is an integer of at least 2;
   provided that L is a C1-6 alkylene group for at least one X; and
   (iii) a dental initiator system.

2. The dental composition according to claim 1, wherein the linker group is a linear or branched monomeric, oligomeric, polymeric or copolymeric group containing nitrogen atoms at the terminal positions.

3. The dental composition according to claim 1, wherein the polymerizable compound of formula (1) contains one or more acidic groups selected from carboxylic acid groups, phosphonic acid groups, sulfonic acid groups or phosphoric acid ester groups.

4. The dental composition according to claim 1, wherein the linker group, A, is a polyamide group obtained by a process comprising the step of a step-growth polymerization of a mixture containing a diamine of the following formula (3) and a compound of the following formula (4) having at least two carboxylic acid groups, said carboxylic acid groups may be present in the form of an anhydride, optionally in the presence of a compound of the following formula (5):

$$R^3(NHR')_y \quad (3)$$

wherein
$R^3$ represents an y-valent $C_{2-20}$ straight-chain, branched or cyclic hydrocarbon group which may optionally contain from 1 to 6 heteroatoms selected from nitrogen, oxygen, or sulphur atoms in the backbone of the hydrocarbon group, and optionally from 1 to 6 functional groups selected from hydroxyl groups, thiol groups and amino groups;
R' represents a hydrogen atom, an aliphatic hydrocarbon group, or a cycloaliphatic hydrocarbon group; and
y represents an integer of at least 2;

$$MOOC—R^4—COOM \quad (4)$$

wherein $R^4$ represents a $C_{1-20}$ straight-chain, branched, cyclic or aromatic hydrocarbon group which may optionally contain from 1 to 6 heteroatoms selected from nitrogen, oxygen, or sulphur atoms in the backbone of the hydrocarbon group, and optionally from 1 to 6 functional groups selected from carboxylic acid groups, hydroxyl groups, thiol groups and amino groups, and the M which may be the same or different, independently represent a hydrogen atom or a metal atom;

(5)

wherein L, $R^1$ and $R^2$ are as defined in claim 1, and Y is a leaving group or Y forms an intramolecular anhydride group together with a carboxyl group present in $R^1$ or $R^2$ and the adjacent carbonyl group.

5. The dental composition according to claim 1, wherein the linker group is a polyoxyalkylene group containing nitrogen atoms at the terminal positions.

6. The dental composition according to claim 1, wherein the polymerizable hydrolysis-stable compound of formula (1) is water-soluble and has a molecular weight of from 300 to 10,000 Da.

7. The dental composition according to claim 1, which contains a fluoride containing compound.

8. The dental composition according to claim 1 wherein the dental particulate filler is an inorganic particulate filler selected from the group of glass, metal oxides, metal hydroxides, salts and mixtures thereof.

9. The dental composition according to claim 1, which provides a shear strength (ISO/TS 11405 (2003)) after curing to dentin or enamel of at least 3 MPa.

10. The dental composition according to claim 1, which is a one-pack composition.

11. The dental composition according to claim 1, wherein $R^1$ and $R^2$ in formula (2) are independent from each other and represent a hydrogen atom, a $C_{1-6}$ alkyl group or a group —$(CH_2)_m$—COOM, wherein M is hydrogen atom or a metal atom, and m is an integer of from 0 to 6.

12. A method comprising using a composition as defined in claim 1 to prepare a dental composition.

13. The method according to claim 12, wherein the dental composition is prepared as a dental restorative or dental prosthetic composition.

14. The dental composition according to claim 1, wherein the compound of formula (1) is further obtained by a process comprising a step of a step-growth polymerization of a mixture containing a diamine of the following formula (3) and a compound of the following formula (4) having at least two carboxylic acid groups, said carboxylic acid groups may be present in the form of an anhydride, in the presence of a compound of the following formula (5):

$$R^3(NHR')_y \quad (3)$$

wherein
R$^3$ represents an y-valent C2-20 straight-chain, branched or cyclic hydrocarbon group which may optionally contain from 1 to 6 heteroatoms selected from nitrogen, oxygen, or sulphur atoms in the backbone of the hydrocarbon group, and optionally from 1 to 6 functional groups selected from hydroxyl groups, thiol groups and amino groups;
R' represents a hydrogen atom, an aliphatic hydrocarbon group, or a cycloaliphatic hydrocarbon group; and
y represents an integer of at least 2;

$$MOOC—R^4—COOM \quad (4)$$

wherein R$^4$ represents a C$_{1-20}$ straight-chain, branched, cyclic or aromatic hydrocarbon group which may optionally contain from 1 to 6 heteroatoms selected from nitrogen, oxygen, or sulphur atoms in the backbone of the hydrocarbon group, and optionally from 1 to 6 functional groups selected from carboxylic acid groups, hydroxyl groups, thiol groups and amino groups and the M which may be the same or different, independently represent a hydrogen atom or a metal atom; and

(5)

wherein L, R$^1$ and R$^2$ are as defined in claim 1, and Y is a leaving group or Y forms an intramolecular anhydride group together with a carboxyl group present in R$^1$ or R$^2$ and the adjacent carbonyl group.

15. The dental composition according to claim 4, wherein the linker group is a linear or branched monomeric, oligomeric, polymeric or copolymeric group containing nitrogen atoms at the terminal positions.

16. The dental composition according to claim 4, wherein the polymerizable compound of formula (1) contains one or more acidic groups selected from carboxylic acid groups, phosphonic acid groups, sulfonic acid groups or phosphoric acid ester groups.

17. A dental composition comprising:
(i) a dental particulate filler;
(ii) a polymerizable hydrolysis-stable compound of the following formula (1)

$$AX_n \quad (1)$$

wherein
A is a linker group containing at least n nitrogen atoms and optionally one or more acidic groups;
X are moieties containing a polymerizable double bond and forming an amide bond with a nitrogen atom of A, which X may be the same or different and are represented by the following formula (2)

(2)

wherein
R$^1$ and R$^2$ are independent from each other and represent a hydrogen atom, a C$_{1-6}$ alkyl group, or a —(CH$_2$)$_m$—Z group, wherein Z is COOM, OPO$_3$M$_2$, PO$_3$M$_2$, or SO$_3$M, M is independently a hydrogen atom or a metal atom, and m is an integer of from 0 to 6;
L is a bond or a C1-6 alkylene group; and
n is an integer of at least 2;
provided that R$^1$ represents a —(CH$_2$)$_m$—Z group for at least one X; and
(iii) a dental initiator system.

18. A dental composition comprising:
(i) a dental particulate filler;
(ii) a polymerizable hydrolysis-stable compound of the following formula (1)

$$AX_n \quad (1)$$

wherein
A is a linker group containing at least one 1,4-cyclohexane bismethylamine group and optionally two or more acidic groups;
X are moieties containing a polymerizable double bond and forming an amide bond with a nitrogen atom of A, which X may be the same or different and are represented by the following formula (2)

(2)

wherein
R$^1$ and R$^2$ are independent from each other and represent a hydrogen atom, a C$_{1-6}$ alkyl group, or a —(CH$_2$)$_m$—Z group, wherein Z is COOM, OPO$_3$M$_2$, PO$_3$M$_2$, or SO$_3$M, M is independently a hydrogen atom or a metal atom, and m is an integer of from 0 to 6;
L is a bond or a C$_{1-6}$ alkylene group; and
n is an integer of at least 2;
provided that at least one X cannot be a (meth)acryl group; and
(iii) a dental initiator system.

* * * * *